United States Patent

Kuhar et al.

Patent Number: 5,380,848
Date of Patent: * Jan. 10, 1995

[54] COCAINE RECEPTOR BINDING LIGANDS

[75] Inventors: Michael J. Kuhar; John W. Boja, both of Baltimore, Md.; Frank I. Carroll, Durham, N.C.; Anita H. Lewin, Chapel Hill, N.C.; Philip Abraham, Cary, N.C.

[73] Assignees: Research Triangle Institute, Research Triangle Park, N.C.; The United States of America as represented by the Department of Health and Human Services, Washington, D.C.

[*] Notice: The portion of the term of this patent subsequent to Jul. 7, 2009 has been disclaimed.

[21] Appl. No.: 233,723

[22] Filed: Apr. 26, 1994

Related U.S. Application Data

[63] Continuation of Ser. No. 792,648, Nov. 15, 1991, abandoned, which is a continuation-in-part of Ser. No. 564,755, Aug. 9, 1990, Pat. No. 5,128,118.

[51] Int. Cl.⁶ .......................................... C07D 451/02
[52] U.S. Cl. ................................. 546/124; 546/125; 546/132
[58] Field of Search .................... 546/124, 125, 132; 424/1.81, 1.85

[56] References Cited

U.S. PATENT DOCUMENTS

| | | | |
|---|---|---|---|
| 3,813,404 | 5/1974 | Clarke et al. | 546/132 |
| 4,179,567 | 12/1979 | Clarke et al. | |
| 5,128,118 | 7/1992 | Carroll et al. | 424/1.1 |

Primary Examiner—Robert L. Stoll
Assistant Examiner—Lara E. Chapman
Attorney, Agent, or Firm—Oblon, Spivak, McClelland, Maier, & Neustadt

[57] ABSTRACT

Novel compounds show high affinity for specific cocaine receptors in the brain, particularly dopamine transporter sites, and have the formula

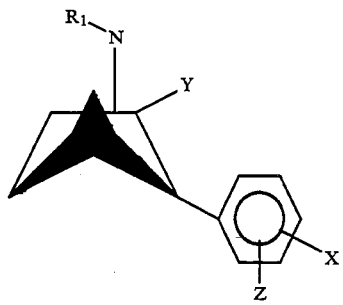

Wherein $Y = CH_2R_3$, $CO_2R_2$ or

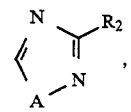

$R_1$ = hydrogen, $C_{1-5}$ alkyl,
$R_2$ = hydrogen, $C_{1-6}$ alkyl, $C_{3-8}$ cycloalkyl, $C_{1-4}$ alkoxy, $C_{1-6}$ alkynyl, halogen or amine,
$R_3$ = OH, hydrogen, $C_{1-6}$ alkyl, $C_{3-8}$ cycloalkyl, $C_{1-4}$ alkoxy, Cl Br, I, CN, $NH_2$, $NHC_{1-6}$ alkyl, $NC_{1-6}$ alkyl, $OCOC_{1-6}$ alkyl, $OCOC_{1-3}$ alkylaryl,
A = S, 0 or NH
X = H, $C_{1-6}$ alkyl, $C_{3-8}$ cycloalkyl, $C_{1-4}$ alkoxy, $C_{1-6}$ alkynyl, halogen, amino, acylamido, and
Z = H, I, Br, Cl, F, CN, $CF_3 NO_2$, $N_3$, $OR_1$, $CO_2NH_2$, $CO_2R_1$, $C_{1-6}$ alkyl, $NR_4R_5$, $NHCOR_5$, $NHCO_2R_6$,
wherein $R_4-R_6$ are each $C_{1-6}$ alkyl.

4 Claims, No Drawings

COCAINE RECEPTOR BINDING LIGANDS

This application is a continuation of U.S. application Ser. No. 7/792,648 filed on Nov. 15, 1991 (now abandoned), which is a continuation in part of Ser. No. 7/564,755 filed Aug. 9, 1990 (now U.S. Pat. No. 5,128,118) which is a continuation in part of U.S. PCT Application PCT/US91/05553 filed on Aug. 9, 1991 in the U.S. PCT Receiving Office and designating the United States.

FIELD OF THE INVENTION

This invention is directed to a class of binding ligands for cocaine and other receptors in the brain. Specifically, a novel family of compounds shows high binding specificity and activity, and, in a radio labeled form, can be used to bind to these receptors, for biochemical assays and imaging techniques.

DISCLOSURE OF PATENT APPLICATIONS

This application claims priority from U.S. patent application Ser. No. 07/564,755, now U.S. Pat. No. 5,128,118, and U.S. PCT Application PCT/US91/05553, filed Aug. 9, 1991, both applications being incorporated herein by reference. In U.S. Pat. No. 5,128,118, there is disclosure of a family of compounds exhibiting particularly high specificity and affinity for cocaine receptors and other neurotransmitter receptors in the brain of the formula:

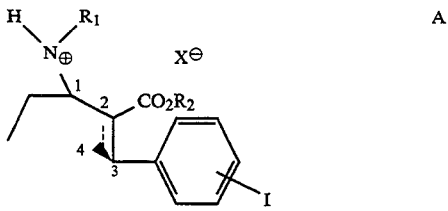

Where the broken line represents an optional chemical bond and the substituents at 2 and 3 may be at any position;

The iodo substituent may be at o, m, p, or multisubstituted;

$R_1 = CH_3$, $CH_2CH=CH_2$, $(CH_2)_2C_6H_5$ $n = 1-4$;

$R_2 = CH_3$, $C_2H_5$, $CH_3(CH_2)_3$, $(CH_3)_2CH$, $C_6H_5$, $C_6H_5CH_2$, $C_6H_5(CH_2)_2$;

X = pharmacologically acceptable anion

Sites of specific interest included cocaine receptors associated with dopamine transporter sites.

Subsequently, in the U.S. PCT Application from which priority is claimed, and which is incorporated herein by reference, the values for $R_1$ and $R_2$ were expanded, such that $R_1$ may be an alkyl of 1–7 carbon atoms, $CH_2CR_3=CR_4R_5$ wherein $R_3$–$R_5$ are each, independently $C_{1-6}$ alkyl, or phenyl compounds of the formula $C_6H_5(CH_2)_y$, wherein $y = 1-6$. The PCT filing also reveals the affinity of these compounds for cocaine receptors associated with serotonin transporters, and confirms, for the first time, that the in vitro binding reported in the earlier-filed application, is confirmed in vivo testing. Specific disclosure for a variety of applications, including using the receptors in both PET and SPECT scanning, wherein either the iodine substituent or one of the carbon groups is radioactive (I-123, 125 or 131 and C11) thus providing methods for scanning for the presence of specific cocaine receptors appears. Such scanning processes may be used to determine physiological conditions, such as Parkinson's Disease, to examine in general the density and distribution of specific cocaine receptors in various parts of the brain and/or body, to determine the efficacy of neurological treatments aimed at halting or reversing the degeneration of specific nerves in the brain, and screening drugs, such as antidepressant drugs.

The affinity of these compounds, as reported in the applications incorporated, is surprisingly high, and compared with prior art compounds, such as [3H]WIN 35,428, the novel compounds of these applications exhibit extremely low $IC_{50}$ values for binding inhibition.

Other compounds exhibiting this type of binding activity and specificity would further advance this art, making it possible to obtain better scanning, with higher reliability, and lower levels.

SUMMARY OF THE INVENTION

Applicants' invention resides in the discovery of a new family of compounds of the formula

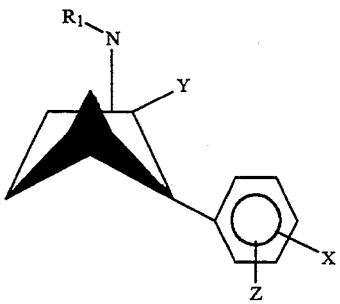

Wherein $Y = CH_2R_3$, $CO_2R_2$ or

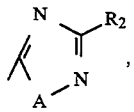

$R_1$ = hydrogen, $C_{1-5}$ alkyl, $R_2$ = hydrogen, $C_{1-6}$ alkyl, $C_{3-8}$ cycloalkyl, $C_{1-4}$ alkoxy, $C_{1-6}$ alkynyl, halogen or amine, $R_3$ = OH, hydrogen, $C_{1-6}$ alkyl, $C_{3-8}$ cycloalkyl, $C_{1-4}$ alkoxy, Cl, Br, I, CN, $NH_2$, $NHC_{1-6}$ alkyl, $NC_{1-6}$ alkyl, $OCOC_{1-6}$ alkyl, $OCOC_{1-3}$ alkylaryl, A = S, O or NH X = H, $C_{1-6}$ alkyl, $C_{3-8}$ cycloalkyl, $C_{1-4}$ alkoxy, $C_{1-6}$ alkynyl, halogen, amino, acylamido, and Z = H, I, Br, Cl, F, CN, $CF_3$ $NO_2$, $N_3$, $OR_1$, $CO_2NH_2$, $CO_2R_1$, $C_{1-6}$ alkyl, $NR_4R_5$, $NHCOR_5$, $NHCO_2R_6$, wherein $R_4$–$R_6$ are each $C_{1-6}$ alkyl.

These compounds exhibit usually high affinity for binding to receptors for the dopamine transporter site, as well as the serotonin transporter site, again based on inhibition of [3H]WIN 35,428 binding. It will be immediately apparent that certain of the compounds embraced within this novel class exhibit iodine substituents, and thus can be made easily radioactive, by substitution of a radioactive iodine, according to the synthesis scheme set forth in the prior applications incorporated herein by reference. In those circumstances where no radioactive iodine is provided, the compounds may be made radioactive by selective use of at least one carbon that is radioactive, e.g., [$^{11}$C].

DETAILED DESCRIPTION OF THE INVENTION:

The compounds of this invention can be prepared according to the synthesis methods described in the parent applications. Additionally, specific synthesis routes and examples are set forth herein.

3β-[3'-Iodo-4'-aminophenyl]tropan-2β-carboxylic Acid Methyl Ester Dihydrochloride (1a)

To a solution of 3β-[4'-aminophenyl]tropan-2β-carboxylic acid methyl ester (300 mg, 1.094 mmol) in glacial AcOH (15mL) was added dropwise ICl (195 mg, 1.201 mmol) at room temperature for 3 h under $N_2$. After removal of solvent, the residue was diluted with $H_2O$, and then the pH was adjusted to basic with concentrated ammonia solution. The mixture was extracted with $CHCl_3$ which was washed with water and brine. After drying over $MgSO_4$, the solvent was evaporated to an oily product which was purified by flash chromatography (hexane-ether, 4:1). The collected fraction was converted to HCl salt with HCl/ether to yield 140 mg (29%) of 3β-[3'-iodo-4'-aminophenyl]tropan-2β-carboxylic acid methyl ester dihydrochloride (1a): mp 170°–173° C.; [α]$^{25}$ −90.9° (c 0.055, MeOH), $^1$H NMR (250 MHZ, $CDCl_3$) δ1.65 (m, 3), 2.09 (m, 2), 2.2 (s, 3, $NCH_3$). 2.45 (m, 1), 2.75 (m, 1, H-2), 2.8 (m, 1, H-3), 3.33 (m, 1, H-5), 3.45 (m, 4, H-1, $OCH_3$), 3.95 (m, 2, $NH_2$), 6.65 (d, 1, J=8.7, ArH, 7.05 (dd, 1, J=8.7, J=1.5, ArH), 7.42 (d, J=1.5, 1, ArH).

Anal. Calcd for $C_{16}H_{21}IN_2O_2$.2 HCL.$H_2O$: C, 39.12; H, 5.13; N, 5.70. Founds C, 39.12, H, 5.16; N, 5.63.

3β-[3'-Iodo-4'-azidophenyl]tropan-2β-carboxylic Acid Methyl Ester HydrochlOride (1b).

To a solution of 3β-[3'-iodo-4'-aminophenyl]tropan-2β-carboxylic acid methyl ester dihydrochloride (1a) (90 mg, 0.1902 mmol) in 1 mL of AcOH (3M) was added an aqueous solution of $NaNO_2$ (17.3 mg, 0.2661 mmol, in 0.5 mL of $H_2O$) at 0° C. After 30 min at this temperature $NaN_3$(19 mg, 0.2754 mmol) in 0.5 mL of $H_2O$ was added dropwise to the reaction mixture and stirred for 30 min at 0° C., then 30 min at room temperature. After removal of all solvent by evaporation, the residue was dissolved in $CHCl_3$ and washed with $H_2O$. The organic layer was dried over $MgSO_4$ and concentrated to give an oil which was converted to HCl salt to yield 64 mg (72.7%) of 3β-[3'-iodo-4'-azidophenyl]tropan-2β-carboxylic acid methyl ester hydrochloride (1b) as a yellowish solid: mp 140°–143° C.; [α]$^{25}$ −97.4° (c 0.115), MeOh); $^1$HNMR (250MHz, $CDCl_3$) δ1.51–1.73 (m, 3) 2.07–2.16 (m, 2), 2.19 (s, 3, $NCH_3$) 2.47 (m, 1), 2.80–2.93 (m, 2), 3.32 (m, 1, H-5), 3.51 (s, 3, $OCH_3$), 3.54 (m, 1, H-1), 7.01 (d, 1, J-7.7, ArH), 7.28 (dd, 1, J=7.77, J=1, ArH), 7.60 (d, 1, J=1, ArH).

Anal. Calcd for $C_{16}H_{19}IN_4O_2$.HCl.$H_2O$: C, 39.98; H, 4.61; N, 11.65. Found: C, 39.96.

Alternative synthesis for related compounds will be apparent to those of ordinary skill in the art. Additional schemes follow hereinbelow.

Synthesis

Treatment of 3β-(4-aminophenyl)tropan-2β-carboxylic acid methyl ester (1) with the appropriate halogen gives 2. Dtazotization of 2 followed by the addition of sodium azide provides the 3-halo-4-azido analog 3 (Scheme 1).

Condensation of anhydroecgonine methyl ester (4) with the appropriate acylamide oxime gives the oxadiazole 5. Addition of the appropriate aryl lithium to 5 gives the cocaine analog 6. The addition of the appropriate aryl magnesium halide to 4gives the analog 7 (Scheme 2).

Hydrolysis of 8 gives the acid 9. Reduction of 9 with diborane gives 10. Treatment of 9 with thionyl chloride, followed by the appropriate amine gives 11. Treatment of 10 with thionyl halide or acylating agent gives 12 and 13, respectively (Scheme 3).

Scheme 1

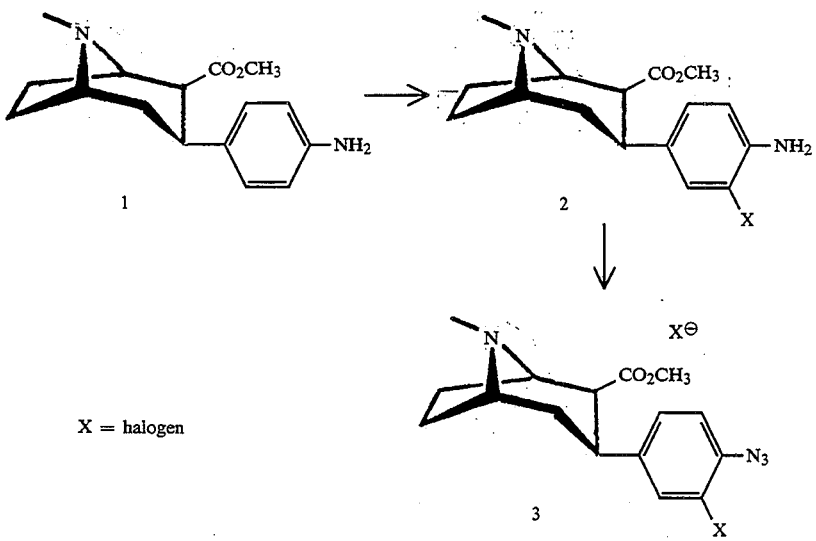

X = halogen

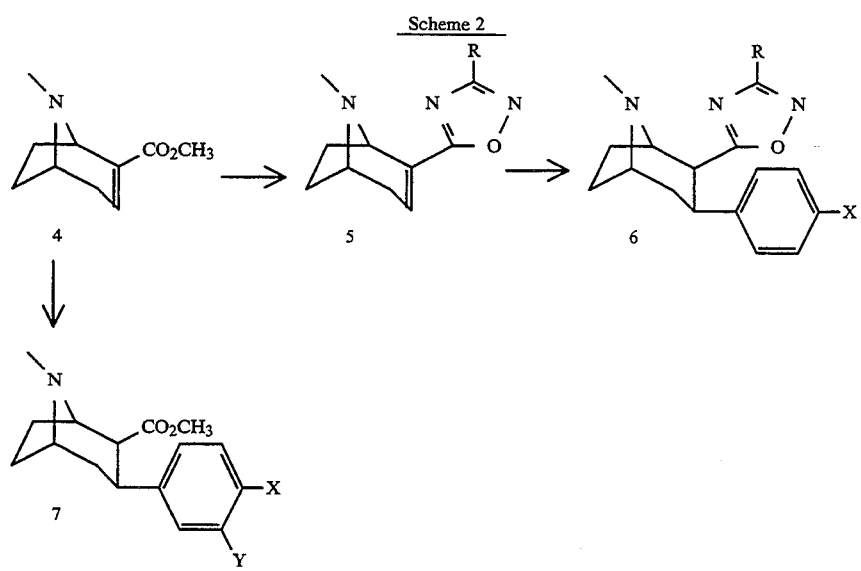

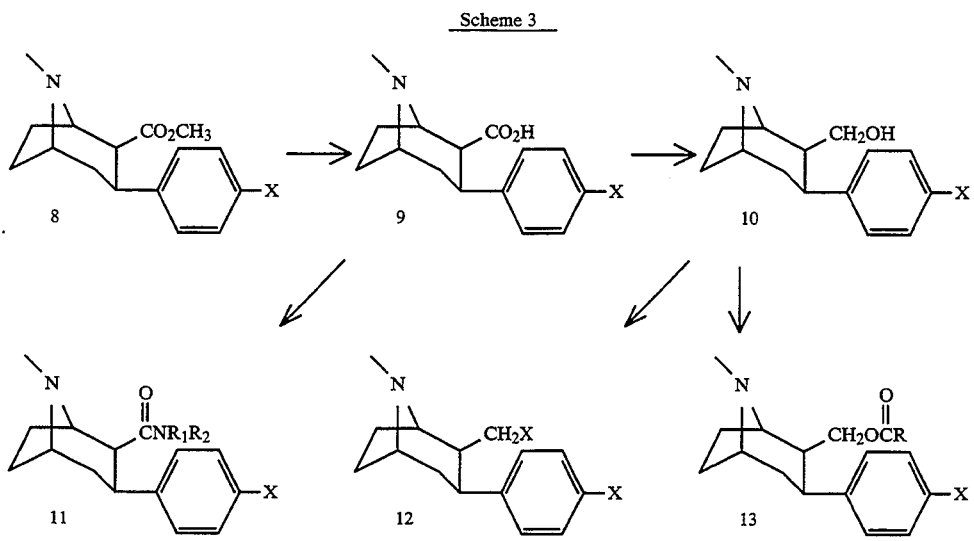

Experimental

2-[3-Methyl-1,2,4-oxadiazol-5-yl]-8-methyl-8-azabicyclo[3.2.1]oct-2-ene (5, R=CH₃)

Acetamide oxime (500 mg, 6.75 mmol) suspended in THF (50 mL) under nitrogen was heated at 60° C. with NaH (132 mg, 5.5 mmol in oil dispersion) for 1 h. Anhydroecgonine methyl ester (2.76 mmol) and 4 Å molecular sieves (2 g) were added and the reaction mixture heated under reflux for 3 h. After cooling, the reaction mixture was filtered and the solvent removed in vacuo. The residue was chromatographed on a silica gel column eluting with CHCl₃—CH₃OH (95:5) to give the free base.

3β-Phenyl-2β-(1,2,4-oxadiazonyl-5-methyl-3-yl)-tropane (6, R=CH₃, X=H)

To an oven-dried, round-bottomed flask equipped with rubber septum and nitrogen inlet was added dry THF (25 mL) and the oxadiazole (5, R=CH₃) (261 mg, 1.27 mmol). The reaction vessel was cooled to −78° C. before adding phenyl lithium (0.636 mL, 1.27 mmol) of a 2M Et₂O solution. The reaction mixture turned dark yellow. Stirring was continued for an additional 2 h before adding brine (10 mL). The crude mixture was extracted with chloroform (3×45 mL), and the combined organic layers were dried (MgSO₄) and concentrated under reduced pressure to yield a yellow solid. Recrystallization from hexanes gave 53 mg (39%) of pure product as white crystals: mp 124°–125° C.; [α]$_D$ +32.1° (c 0.14, MeOH); ¹H NMR (250 MHz, CDCl) δ1.55–1.84 (m, 2), 1.88–1.98 (m, 2), 1.99–2.18 (m, 1), 2.24 (s, 3), 2.33 (s, 3), 2.47–2.58 (m, 1), 3.31–3.37 (t, 1, J=7.0 Hz), 3.56–3.62 (t, 1, J=5.7 Hz), 3.69–3.79 (ABq, 1, J=16.1, 8.0 Hz), 4.16–4.22 (t, 1, J=7.5 Hz), 7.05–7.14 (m, 5).

Anal. Calcd for C₁₇H₂₁N₃O: C, H, N.

3β-(3-Bromo-4-aminophenyl)trpane Carboxylic Acid Methyl Ester (3, X=Br)

To a round-bottomed flask containing N,N-dimethylformamide (2.5 mL) was added 3β-(4-aminophenyl)tropane carboxylic acid methyl ester (100 mg, 0.365 mmol) and N-bromosuccinimide (64.5 mg, 0.365 mmol) under a stream of nitrogen gas at ambient temperature. The resulting solution immediately turned deep red. After stirring for an additional 2.5 h, water (5 mL) was added, and the crude reaction mixture was extracted with chloroform (3×25 mL). The combined organic extract was dried (MgSO$_4$) and concentrated under reduced pressure to yield the product as a brown oil. Flash chromatography (5% methanol-chloroform) afforded 42 mg (33%) of pure product as a yellow oil: mp of HCl salt 194° C. dec; $[\alpha]_D$ −87.7° (c 0.09, MeOH); $1_H$ NMR (250 MHz, DMSO) δ2.51-2.38 (m, 4), 3.39 (s, 3), 3.66-3.77 (td, 2, J=12.5, 2.9 Hz) 4.17-4.59 (br s, 2), 4.67 (s, 3), 4.69-4.96 (br s, 2), 5.92 (br s, 2), 7.96-8.68 (m, 3H).

Anal. Calcd for $C_{16}H_{21}BrN_2O_2.2$ HCl.2 $H_2O$): C, H, N.

General Procedure for Hydrolysis of 3β-[4-Halophenyl]tropan-2β-car-boxylic Acid Methyl Esters The methyl ester (1.0 mmol) was dissolved in 20 mL 50% aqueous dioxane and heated to reflux. After 6 h, the solvent was evaporated and the residue crystallized from MeOH-Et$_2$O except as noted.

3β-[4-Iodophenyl]tropan-2β-carboxylic Acid (9, X=I)

The starting methyl ester (0.52 mmol, 0.20 g) gave 0.137 g (71%) of the acid as a white solid: top, 318°–320° C.; $[\alpha]_D^{25}$ −79.3 (c 0.55, CH$_3$OH); $1_H$ NMR (CDCl$_3$) δ1.78 (m, 1), 2.02 (m, 2), 2.34 (m, 2), 2.61 (s, 3, —NCH$_3$), 2.7 (m, 2), 3.12 (m, 1), 3.73 (m, 2), 7.03 (d, 2, ArH), 7.62 (d, 2, ArH).

Anal. Calcd for $C_{15}H_{18}INO_2$: C, 48.53; H, 4.89; N, 3.77. Found: C, 48.42; H, 4.89; N, 3.71.

3β-[4-Bromophenyl]tropan-2β-carboxylic Acid (9, X=Br)

The starting ester (0.38 g, 1.1 mmol) gave 0.208 g (58%) of the acid as a white solid: mp 304°–305° C.; $[\alpha]_D$ −85.1° (c 0.55, CH$_3$OH); $^1H$ NMR (CDCl$_3$) δ1.79 (m, 1), 2.05 (m, 2), 2.33 (m, 2), 2.65 (s, 3, —NCH$_3$), 2.76 (m, 2), 3.315 (m, 1), 3.77 (m, 2), 7.16 (d 2, ArH), 7.42 (d 2, ArH).

Anal. Calcd for $C_{15}H_{18}BrNO_2$: C, 55.57; H, 5.59; N, 4.32; Br, 24.65. Found: C, 55.36; H, 5.63; N, 4.28; Br, 24.53.

3β-[4-Fluorophenyl]tropan-2β-carboxlic Acid (9, X=F)

The starting methyl ester (0.60 g, 2.2 mmol) gave 0.360 g (62%) of the acid as a white solid: mp 299°–300° C.; $[\alpha]_D^{25}$ −92.5° (c 0.89, CH$_3$OH); $1_H$ NMR (CDCl$_3$) δ1.80 (m, 1), 2.06 (m, 2), 2.36 (m, 2), 2.66 (s, 3, —NCH$_3$), 2.69 (m, 1), 2.79 (m, 1), 3.18 (m, 1), 3.79 (m, 2), 6.99 (m, 2, ArH), 7.25 (m, 2, ArH).

Anal. Calcd for $C_{15}H_{18}FNO_2$: C, 68.42; H, 6.89; N, 5.32. Found: C, 68.29; H, 6.93; N, 5.26.

3β-[4-Chlorophenyl]tropan-2β-carboxlic Acid (9, X=Cl)

The starting methyl ester (5.0 g, 6.91 mmol) gave 3.5 g (74%) of the acid (from H$_2$O) as a white solid: mp 300°–301° C.; $[\alpha]_D^{25}$ −108.0° (c 0.10, CH$_3$OH); $^1H$ NMR (CDCl$_3$) δ1.57–1.9 (m, 4), 2.25 (m, 2), 2.45 (s, 3, NCH$_3$), 2.52 (m, 1), 3.12 (m, 1, H-2), 3.55 (m, 2, H-1, H-5), 7.19 (dd, 4, ArH).

Anal. Calcd for $C_{15}H_{18}ClNO_2.0.25$ $H_2O$: C, 63.38; H, 6.56; N, 4.93. Found: C, 63.78; H, 6.56; N, 4.97.

General Procedure for Preparation of 3β-[4-Halophenyl]2β-hydroxy-methylpropane The 2β-carboxylic acid (1.0 mmol) was suspended in dry THF (20 mL) at 0° C. under N$_2$. A solution of BH$_3$ in THF (4.0 mL of 1M solution, 4.0 mmol) was added by syringe. After 3 h, the reaction was quenched with conc. HCl (1.0 mL) and stirred for 30 min. The solvent was evaporated and the residue partitioned between dilute NH$_4$OH and CH$_2$Cl$_{12}$. The aqueous phase was further extracted with CH$_2$Cl$_2$ (3×50 mL). The organic extract was dried over Na$_2$SO$_4$, filtered and evaporated leaving a white solid. This was chromatographed on a silica gel flash column eluting with Et$_2$O-Et$_3$N (9:1). The sample from the column was crystallized from pentane, except as noted.

3β-[4-Iodophenyl]-2β-hydroxymethyltropane (10, X=I)

The starting 2β-carboxylic acid (0.100 g, 0.270 mmol) gave 0.055 g (57%) of the product as a white crystalline solid: mp 104°–105° C.; $[\alpha]_D^{25}$ −54.6 (c 0.5, 2), 2.17(m, 2), 2.27 (s, 3, NCH$_3$), 2.48 (m, 1), 3.03 (m, 1), 3.34 (m, 2), 3.45 (m, 1), 3.75 (m. 1), 7.13 (d, 2, ArH), 7.63 (d, 2, ArH).

Anal. Calcd for $C_{15}H_{20}INO$: C, 50.43; H, 5.64; N, 3.92. Found: C, 50.52; H, 5.67; N, 3.84.

3β-[4-Bromopheny]2β-hydroxymethyltropane (10, X=Br)

The starting 2β-carboxylic acid (0.150 g, 0.463 mmol) gave 0.045 g (315) of the product as a white crystalline solid: mp 92°–93° C.; $[\alpha]_D^{25}$ −55.8° (c 0.5, CHCl$_3$); $^1H$ NMR (CDCl$_3$) δ1.46 (m, 1), 1.62 (m, 1), 1.72 (d, 2), 2.17 (m, 2), 2.27 (s, 3, NCH$_3$), 2.50 (m, 1), 3.03 (m, 1), 3.34 (m, 2), 3.45 (m, 1), 3.76 (m, 1), 7.25 (d, 2, ArH), 7.43 (d, 2, ArH).

Anal. Calcd for $C_{15}H_{20}BrNO$: C, 58.07; H, 6.50; N, 4.52; Br, 25.76. Found: C, 57.97; H, 6.55; N, 4.45; Br, 25.83.

3β-[4-Fluorophenyl]-2β-hydroxymethyltropane (10, X=F)

The starting 2β-carboxylic acid (0.263 g, 1.0 mmol) gave 0.140 g (56%) of the product as a white crystalline solid: mp 79°–80° C.; $[\alpha]_D^{25}$ −59.8° (c 0.5, CHCl$_3$); $^1H$ NMR (CDCl$_3$) δ1.45 (m, 1), 1.63 (m, 1), 1.72 (d, 2), 2.16 (m, 2), 2.27 (s, 3, NCH$_3$), 2.49 (m, 1), 3.07 (m, 1), 3.34 (m, 2), 3.45 (m, 1), 3.76 (m, 1), 6.99 (m, 2, ArH), 7.32 (m, 2, ArH).

Anal. Calcd for $C_{15}H_{20}FNO$: C, 72.26; H, 8.08; N, 5.62. Found: C, 72.17; H, 8.10; N, 5.61.

3β-[4-Chlorophenyl]-2β-hydroxymethyltropane (10, X=Cl)

The starting 2β-carboxylic acid (0.950 g, 3.4 mmol) gave 0.30 g (33%) of the product as an off-white crystalline solid: mp 104°–106° C.; $[\alpha]_D^{25}$ −82.4° (c 0.21, CH$_3$OH); $^1H$ NMR (CDCl$_3$) δ1.45 (m, 1), 1.67 (m, 3), 2.17 (m, 2), 2.25 (s, 3, NCH$_3$), 2.50 (m, 1), 3.05 (m, 1, H-3), 3.30 (m, 2), 3.40 m, 1, H-1), 3.72 (dd, 1), 7.29 (m, 4, ArH).

Anal. Calcd for $C_{15}H_{20}ClNO$: C, 67.78; H, 7.59; N, 5.27. Found: C, 67.63; H, 7.69; N, 5.25.

3β-[p-Chlorophenyl]-2β-acetoymethyltropane (13, X=Cl)

To a flask containing acetic anhydride (10 mL) in dry pyridine (5 mL) at ambient temperature was added 3β-(p-chlorophenyl)-2β-hydroxymethyltropane (95 mg, 0.32 mmol). The reaction mixture was maintained at room temperature for 2 h before diluting with water (10 mL) and adjusting the pH of the aqueous phase to 14. After extraction of the aqueous phase with chloroform (3×25 mL), the organic layers were combined, dried (MgSO$_4$) and concentrated under reduced pressure to yield the crude product as a yellow oil. Flash chromatography (CHCl$_3$—MeOH, 9:1) yielded 45 mg (41%) of pure product as a colorless oil: mp of HCl salt 202° C. dec; [α]$_D$ −57.1° (c 0.070, MeOH); $^1$H NMR (250 MHz, CDCl$_3$) δ2.02 (s, 3), 2.17–2.59 (m, 6), 2.87 (s, 3), 3.49–3.69 (m, 2), 3.99–4.22 (m, 4), 7.27–7.41 (m, 4).

Anal. Calcd for C$_{17}$H$_{22}$ClNO$_2$.HCl.0.25 H$_2$O: C, H, N.

3β-9-(p-Chlorophenyl)-2β-(N-methylcarbamoyl)tropane (11, R=CH$_3$, R$_2$=H, X=Cl)

To a flask containing thionyl chloride (10 mL) at 0° C. was added 3β-(p-chlorophenyl)tropane-2β-carboxylic acid (183 mg, 0.0715 mmol). The mixture was maintained at 0° C. for 4 h before concentrating under reduced pressure. The brown residue was dissolved in methylene chloride (10 mL) and cooled to 0° C. before adding methylamine (5 mL). Stirring was continued for 15 min after which the excess methylamine was allowed to evaporate. The brown residue was diluted with water (25 mL) and extracted with CHCl$_3$ (3×25 mL). The combined extracts were dried (MgSO$_4$) and concentrated under reduced pressure to give the crude product as a brown oil. Flash chromatography (CHCl$_3$—MeOH, 9:1) yielded 72 mg (37%) of pure product as a yellow oil: mp HCl salt 138° C.; [α]$_D$ −96.9° (c 0.170, MeOH); $^1$H NMR (250 MHz, CDCl$_3$) δ1.55–1.88 (m, 5), 2.07–2.28 (m, 2), 2.31 (s, 3), 2.35–2.55 (m, 1), 2.69 s, 3), 3.11–3.33 (m, 1), 3.40–3.49 (br s, 1), 7.14–7.26 (m, 4).

Anal. Calcd for C$_{16}$H$_{21}$ClN$_2$O.HCl.0.75 H$_2$O): C, H, N.

3β-(p-Chlorophenyl)-2β-chloromethyltropane (12, X=Y=Cl)

To a flask containing thionyl chloride (5 mL, ) was added 3β-(p-chlorophenyl)-2p-hydroxymethyltropane (64 mg, 0.24 mmol). The reaction mixture was maintained at reflux for 2 h before carefully diluting with water and adjusting the pH of the aqueous phase to 14 with conc. ammonium hydroxide. The aqueous layer was extracted with CHCl$_3$ (3×25 mL). The organic layers were combined, dried (MgSO$_4$), and concentrated under reduced pressure to yield the crude product as a brown oil. Flash chromatography (CHCl$_3$—MeOH, 9:1) yielded 33 mg (52%) of pure product as a colorless oil: mp of HCl salt 208° C.; [α]$_D$ −63.9° (c 0.155, MeOH); $^1$H NMR (250 MHz, CDCl$_3$) δ 1.05–2.50 (m, 6), 2.69 (s, 3), 2.88–3.16 (m, 2), 3.25–3.52 (m, 1), 3.78–3.89 (br s, 1), 4.02–4.15 (br s, 1), 4.55 (t, 1, J=12.3 Hz), 7.01–7.59 (m, 4).

Anal. Calcd for C$_{15}$H$_{19}$Cl$_2$N.HCl: C, H, N.

3β-(3,4-Dichlorophenyl)-2β-chloromethyltropane (7X=Y=Cl)

To a three-neck, round-bottomed flask containing freshly distilled ether (125 mL) and magnesium turnings (268 mg, 11.0 mmol) was added 3,4-dichlorolodobenzene (2.26 g, 8.27 mmol). After 2 h, the reaction flask was equipped with a mechanical stirrer, and the Grignard reagent was cooled to −55° C. before adding anhydroecgontne methyl ester (500 mg, 2.75 mmol). The resulting solution was stirred for an additional 2.5 h before being cooled to −78° C. After 1 h, 2 mL of trifluoroacetic acid was added to the solution followed by 2 h of stirring. The quenched reaction mixture was then diluted with 1N HCl (100 mL) and extracted with ether (3×100 mL). The ethereal layers were discarded, and the aqueous layer was basified with conc. ammonium hydride and then extracted with chloroform (3×50 mL). The combined organic layers were dried (MgSO$_4$) and concentrated under reduced pressure to yield the crude product as a colorless oil. Flash chromatography (ethertriethylamine, 9:1) yielded 71 mg (9.0%) of pure product: $^1$H NMR (250 MHz, CDCl$_3$) δ1.52–1.76 (m, 2), 1.81–1.95 (m, 2), 1.96–2.22 (m, 2), 2.38 (s, 3), 3.07–3.15 (br s, 2), 3.21–3.32 (br s, 1), 3.45–3.65 (m, 1), 3.50 (s, 3), 7.10–7.38 (m, 3).

Anal. Calcd for C$_{16}$H$_{19}$Cl$_2$NO$_2$.HCl): C, H, N.

3β-(4-Chloro-3-methyphenyl)-2β-chloromethyltropane (7, X=Cl, Y=CH$_3$)

To a three-neck, round-bottomed flask containing freshly distilled ether (125 mL) and magnesium turnings (200 mg, 8.25 mmol) was added 4-chloro-3-methylbromobenzene (1.69 g, 8.25 mmol). After 2 h, the reaction flask was equipped with a mechanical stirrer, and the Grignard reagent was cooled to −55° C. before adding anhydroecgonine methyl ester (500 mg, 2.75 mmol). The resulting solution was stirred for an additional 2.5 h before being cooled to −78° C. After 1 h, 2 mL of trifluoroacetic acid was added to the solution followed by 2 h of stirring. The quenched reaction mixture was then diluted with of 1N HCl (100 mL) and washed with ether (3×100 mL). The aqueous layer was basified with conc. ammonium hydroxide and extracted with CHCl$_3$ (3×50 mL). The combined organic layers were dried (MgSO$_4$) and concentrated under reduced pressure to yield the crude product as a colorless oil. Flash chromatography (ether-triethylamine, 9:1) yielded 45 mg (5.0%) of pure product: $^1$H NMR (250 MHz, CDCl$_3$) δ1.51–1.83 (m, 2), 1.97–2.21 (m, 2), 2.20 is, 3), 2.45–2.59 (td, 1, J=9.5, 2.6 Hz, 2.82–3.02 (m, 3), 3.34–3.40 (br s, 1), 3.51 (s, 3), 3.52–3.61 (br s, 1), 7.00–7.23 (m, 3).

Anal. Calcd for C$_{17}$H$_{22}$ClNO$_2$.HCl.2 H$_2$O: C, H, N.

3β-(3′-Methyl-4′-fluorophenyl)tropan-2β-carboxylic Acid Methyl Ester (7, X=F, Y=CH$_3$)

The title compound was prepared by modification of a reported procedure used to prepare other similar compounds.[ref] Thus, using anhydroecgonine methyl ester (500 mg, 2.76 mmol) and 3-methyl-4-fluorophenyl magnesium bromide (prepared from 200 mg of magnesium metal and 1 mL of 3-methyl-4-fluoro-1-bromobenzene) yielded 234 mg (29%) of the title compound. The hydrochloride salt had mp 163°–165° C.; [α]$_D^{25}$ −103.8° (c 0.08, MeOH); $^1$H NMR of free base of 41 (250 MHz, CDCl$_3$) δ1.67 (m, 3), 2.15 (m, 2), 2.19 is, 3, CH$_3$), 2.20 is, 3, NCH$_3$), 2.55 (m, 2), 2.87 (m, 1, H-2), 2.93 (m, 1, H-3), 3.35 (m, 1, H-5), 3.49 (s, 3, OCH3), 3.55 (m, 1, H-1), 6.85, 6.97 (m, 3, C6H3).

Anal. Calcd for $C_{17}H_{23}ClFNO_2 \cdot 1.5 H_2O$: C, 57.54; H, 7.39; N, 3.95. Found: C, 57.88; H, 7.21; N, 4.20.

[$^3$H]WIN 35,428 Radioligand Binding

Rat striata from male Sprague-Dawley rats (250–350 g) were rapidly dissected, frozen, and stored at −70° C. until used. The frozen rat striata were homogenized in 20 volumes of 10 mM phosphate buffer (pH 7.4) containing 0.32M sucrose using a polytron (setting 6) for 10 sec. The homogenate was centrifuged for 10 min at 50,000×g, the resulting pellet was washed in buffer, recentrifuged, and resuspended to a tissue concentration of 10.0 mg/mL. Binding assays were carried out in a total volume of 0.5 mL containing 0.5 nM [$^3$H]WIN 35,428 and 1.0 mg tissue. The suspensions were incubated for 2 h on ice. Incubations were terminated by filtration with three 5 mL washes through Whatman GF/B filters previously soaked in 0.05% polyethylenimine using a Brandel M48R filtering manifold (Brandel Instruments, Gaithersburg, Md). Radioactivity was counted in 5 mL of scintillation cocktail in a Beckman LS 3801 liquid scintillation counter with an efficiency of approximately 50%. Nonspecific binding of [$^3$H]WIN 35,428 was defined by the presence of 30 μM (−)-cocaine. Under these conditions, nonspecific binding was approximately 5–8% of total binding. IC$_{50}$ values were determined from competition curves of 10–12 points utilizing the curve fitting program EBDA. Mean values and standard errors were calculated from 3–4 assays for each test drug.

Tissue Preincubation with Irreversible Agents

Tissue was prepared as described above, and the final homogenate was incubated for 60 min with either drug or vehicle as control for 60 min on ice in the above buffer. Following the 60 min incubation period, all compounds containing an azido group were then exposed to UV light (2800 Å) for 40 sec. The incubation of all compounds was terminated by centrifugation at 50,000×g for 10 min. The resulting pellet was resuspended to a concentration of 10 mg/mL, and an aliquot was removed (0 washes). This procedure was repeated for a total of 3 washes. Residual [$^3$H]WIN 35,428 binding was determined as described above. Data are expressed as the percent of specific control binding.

Testing of various compounds within the described class has given remarkably high binding values. Thus, as reported in the parent applications, receptor binding activity can be determined by degree of inhibition of the binding of [$^3$H]WIN 35,428. In such assays, the ligand of interest is assigned a IC$_{50}$ value, when incubated in a 10 nM phosphate buffer, pH 7.4, containing 0.32$^m$ sucrose, with 0.5 nM [$^3$H]WIN 35,428 for a two hour period of time. After that, the radioactivity bound to the substrate is measured. As reported in U.S. application Ser. No. 07/564,755, on binding to a dopamine transporter receptor site, cocaine gave a IC$_{50}$ of 89.00 nM, WIN 35,428 gave a value of 14.00 nM and a compound representative of the subject matter claimed in that application, 3β-[4-iodophenyl]-tropane-2β-carboxylic acid methyl ester tartrate gave a IC$_{50}$ value of 0.25 nM. In similar assays, values of 1.35 and 4.93 nM were obtained for compounds within the class set forth above, particularly those compounds bearing a carboxylic acid moiety, or a heterocyclic moiety. Similar values may be obtained for the remaining members of the class.

When bearing an appropriate radioactive label, such as $^{11}$C or $^{123}$I, $^{125}$I or $^{131}$I, these compounds, preferential binders to dopamine transporter and serotonin transporter binding sites, can be used as imaging agents for both positron emission tomography (PET) as well as single photon emission computed tomography (SPECT). PET may require the [$^{11}$C] labeled form of the drug, while radioactive iodine-labeled compounds may be used in SPECT scanning.

As noted, such scanning has a variety of utilities. The actual density and distribution of cocaine receptors in various parts of the brain and CNS is of interest, and can be mapped through the use of these compounds. Additionally, as noted above, identification of degeneration of nerve terminals, corresponding to a loss of dopamine transporter sites, can be determined by this scanning, to diagnose Parkinson's Disease. In addition, progression of the disease, and efficacy of treatment, can be monitored by such scanning. Similarly, degeneration of specific nerves in the brain due to exposure to various toxins can be detected or monitored by the scanning made possible by these compounds.

As an additional use, drugs having high affinity for the transporter sites bound to by these compounds, particularly serotonin and dopamine transporter sites, can be screened, using these compounds, in the identified scanning methods. The scanning itself is conventional, given the use of these compounds, and does not constitute an aspect of the invention per se. Affinity values for representative compounds are given in the following table.

TABLE

Potencies of Cocaine and Analogs in Inhibiting Binding of [$^3$H]-3β-(4-Fluorophenyl)tropan-2β-carboxylic Acid Methyl Ester (WIN 35,428)

| Compound | | IC$_{50}$ (nM) |
|---|---|---|
| Cocaine | | 102 |
| 2 | (X = I) | 1.35 |
| 3 | (X = I) | 4.93 |
| 6 | (R = CH$_3$, X = H) | 48 |
| 7 | (X = Y = Cl) | 0.79 |
| 7 | (X = Cl, Y = CH$_3$) | 0.81 |
| 9 | (X = Br) | 279 |
| 9 | (X = I) | 474 |
| 9 | (X = Cl) | 2070 |
| 9 | (X = F) | 2740 |
| 10 | (X = Br) | 1.49 |
| 10 | (X = Cl) | 1.53 |
| 10 | (X = I) | 2.2 |
| 10 | (X = F) | 47.3 |
| 11 | (R$_1$ = CH$_3$, R = H, X = Cl) | 12.4 |
| 12 | (X = Y = Cl) | 2.64 |
| 13 | (R = CH$_3$, X = Cl) | 1.6 |

This invention has been described in both generic terms, and by reference to specific description. No specific description or example is considered binding, unless so identified. Alternate forms and methods will occur to those of ordinary skill in the art, without the exercise of inventive faculty, and remain within the scope of this invention, save as limited by the claims set forth below.

What is claimed is:

1. A compound of the formula below,

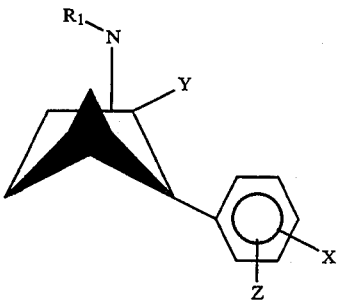

wherein Y=CH₂R₃, CO₂R₂ or

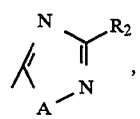

$R_1$ = hydrogen, $C_{1-5}$ alkyl, $R_2$ = hydrogen, $C_{1-6}$ alkyl, $C_{3-8}$ cycloalkyl, $C_{1-4}$ alkoxy, $C_{1-6}$ alkynyl, halogen or amine, $R_3$ = OH, hydrogen, $C_{1-6}$ alkyl, $C_{3-8}$ cycloalkyl, $C_{1-4}$ alkoxy, Cl, Br, I, CN, $NH_2$, $NHC_{1-6}$ alkyl, $NC_{1-6}$ alkyl, $OCOC_{1-6}$ alkyl, $OCOC_{1-3}$ alkylaryl, A = S, 0 or NH X = H, $C_{1-6}$ alkyl, $C_{3-8}$ cycloalkyl, $C_{1-4}$ alkoxy, $C_{1-6}$ alkynyl, halogen, amino, acylamido, and Z = H, I, Br, Cl, F, CN, $CF_3$ $NO_2$, $N_3$, $OR_1$, $CO_2NH_2$, $CO_2R_1$, $C_{1-6}$ alkyl, $NR_4R_5$, $NHCOR_5$, $NHCO_2R_6$, wherein $R_4$–$R_6$ are each $C_{1-6}$ alkyl and wherein Z or $R_3$ comprises at least one iodine or $^{11}C$ atom which is radioactive.

2. The compound of claim 1, wherein said radioactive atom is ($^{11}C$).

3. The compound of claim 1, wherein said compound bears an iodine atom, and said iodine atom is radioactive, and selected from the group consisting of $^{123}I$, $^{125}I$ and $^{131}I$.

4. A substantially pure preparation of a compound of the formula below,

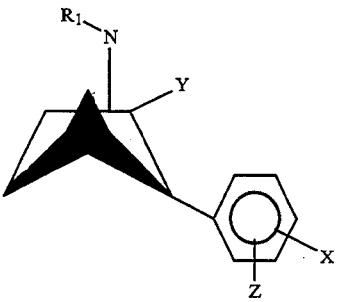

wherein Y=CH₂R₃, CO₂R₂or

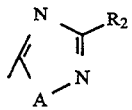

$R_1$ = hydrogen, $C_{1-5}$ alkyl, $R_2$ = hydrogen, $C_{1-6}$ alkyl, $C_{3-8}$ cycloalkyl, $C_{1-4}$ alkoxy, $C_{1-6}$ alkynyl, halogen or amine, $R_3$ = OH, hydrogen, $C_{1-6}$ alkyl, $C_{3-8}$ cycloalkyl, $C_{1-4}$ alkoxy, Cl, Br, I, CN, $NH_2$, $NHC_{1-6}$ alkyl, $NC_{1-6}$ alkyl, $OCOC1-6$ alkyl, $OCOC_{1-3}$ alkylaryl, A = S, 0 or NH X = H, $C_{1-6}$ alkyl $C_{3-8}$ cycloalkyl, $C_{1-4}$ alkoxy, $C_{1-6}$ alkynyl, halogen, amino, acylamido, and Z = H, I, Br, Cl, F, CN, $CF_3$ $NO_2$, $N_3$, $OR_1$, $CO_2NH_2$, $CO_2R_1$, $C_{1-6}$ alkyl, $NR_4R_5$, $NHCOR_5$, $NHCO_2R_6$, wherein $R_4$–$R_6$ are each $C_{1-6}$ alkyl and wherein said compound bears at least one radioactive atom selected from the group consisting of radioactive iodine as substituent Z or $R_3$, and radioactive carbon atoms.

* * * * *

UNITED STATES PATENT AND TRADEMARK OFFICE
CERTIFICATE OF CORRECTION

PATENT NO.   : 5,380,848
DATED        : January 10, 1995
INVENTOR(S)  : Michael J. KUHAR, et al.

It is certified that error appears in the above-indentified patent and that said Letters Patent is hereby corrected as shown below:

On the title page, Item [73], the Assignee should read:

--Research Triangle Institute, Research Triangle Park, N.C.;
The United States of America as represented by the Department
of Health and Human Services, Washington, D.C.--

Signed and Sealed this

Twenty-ninth Day of August, 1995

Attest:

BRUCE LEHMAN

*Attesting Officer*    *Commissioner of Patents and Trademarks*